(12) United States Patent
Sekiguchi et al.

(10) Patent No.: US 12,394,039 B2
(45) Date of Patent: Aug. 19, 2025

(54) LUBRICATING OIL DEGRADATION EVALUATION SYSTEM AND LUBRICATING OIL DEGRADATION EVALUATION METHOD

(71) Applicant: IDEMITSU KOSAN CO., LTD., Chiyoda-ku (JP)

(72) Inventors: Hiroki Sekiguchi, Ichihara (JP); Genki Okuyama, Chiba (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 541 days.

(21) Appl. No.: 17/598,393

(22) PCT Filed: Mar. 30, 2020

(86) PCT No.: PCT/JP2020/014662
§ 371 (c)(1),
(2) Date: Sep. 27, 2021

(87) PCT Pub. No.: WO2020/203995
PCT Pub. Date: Oct. 8, 2020

(65) Prior Publication Data
US 2022/0156909 A1    May 19, 2022

(30) Foreign Application Priority Data

Mar. 29, 2019 (JP) ................. 2019-068998

(51) Int. Cl.
*G06T 7/00* (2017.01)
*G01N 33/28* (2006.01)

(52) U.S. Cl.
CPC ......... *G06T 7/001* (2013.01); *G01N 33/2888* (2013.01); *G06T 2207/20081* (2013.01);
(Continued)

(58) Field of Classification Search
CPC ........... G06T 7/001; G06T 2207/20081; G06T 2207/20084; G06T 2207/30108;
(Continued)

(56) References Cited

U.S. PATENT DOCUMENTS

| 5,517,575 A * | 5/1996 | Ladewski ............ G01B 11/303 356/601 |
| 7,542,138 B2 * | 6/2009 | Gardner, Jr. .......... G01J 3/0224 356/244 |

(Continued)

FOREIGN PATENT DOCUMENTS

| CN | 102667461 A | 9/2012 |
| CN | 105758862 A | 7/2016 |

(Continued)

OTHER PUBLICATIONS

Office Action issued Jun. 27, 2023, in corresponding Japanese Patent Application No. 2021-512130 (with English Translation), 11 pages.

(Continued)

*Primary Examiner* — Roy M Punnoose
(74) *Attorney, Agent, or Firm* — Oblon, McClelland, Maier & Neustadt, L.L.P.

(57) ABSTRACT

Provided are a lubricating oil degradation evaluation system and a lubricating oil degradation evaluation method capable of immediately evaluating degradation and a contamination state of a lubricating oil by including: a storage unit 10 that stores evaluation reference data 100 regarding evaluation of degradation of a lubricating oil; a creation unit 20 that acquires imaging data 210 of an evaluation lubricating oil serving as an evaluation target captured by an imaging apparatus 21 having a communication function and creates image analysis data 200 regarding degradation of the evaluation lubricating oil from the imaging data 210; and an evaluation unit 30 that creates an evaluation result 300 of a (Continued)

degree of degradation of the evaluation lubricating oil from the image analysis data 200 on the basis of the evaluation reference data 100.

6 Claims, 4 Drawing Sheets

(52) U.S. Cl.
CPC .............. *G06T 2207/20084* (2013.01); *G06T 2207/30108* (2013.01)

(58) Field of Classification Search
CPC .. G01N 33/2888; G01N 21/25; G01N 21/251; G01N 21/94; G01N 21/27; G01J 3/2823
See application file for complete search history.

(56) References Cited

U.S. PATENT DOCUMENTS

| | | | |
|---|---|---|---|
| 2010/0206056 A1* | 8/2010 | Horstmeyer | B01D 39/18 73/53.07 |
| 2012/0229151 A1* | 9/2012 | Katafuchi | F01M 11/10 324/672 |
| 2013/0250322 A1* | 9/2013 | Kawabata | H04N 1/6058 358/1.9 |
| 2015/0138538 A1 | 5/2015 | Sakurai | |
| 2015/0177219 A1 | 6/2015 | Ohnuma et al. | |
| 2016/0069856 A1 | 3/2016 | Gorritxategi et al. | |
| 2016/0223469 A1* | 8/2016 | Horstmeyer | G01N 21/94 |
| 2016/0321824 A1* | 11/2016 | Karasawa | G01N 21/80 |
| 2018/0299355 A1* | 10/2018 | Young | G01N 33/2858 |
| 2018/0299375 A1* | 10/2018 | Young | G06N 5/01 |
| 2019/0101473 A1 | 4/2019 | Young et al. | |
| 2019/0162711 A1* | 5/2019 | Gaemers | G01N 33/2888 |
| 2019/0226947 A1 | 7/2019 | Young et al. | |

FOREIGN PATENT DOCUMENTS

| | | | |
|---|---|---|---|
| CN | 106908452 A | | 6/2017 |
| CN | 108959769 A | | 12/2018 |
| JP | 7-140074 A | | 6/1995 |
| JP | 8-62207 A | | 3/1996 |
| JP | 2004-84498 A | | 3/2004 |
| JP | 2012-13675 A | | 1/2012 |
| JP | 2015/99116 A | | 5/2015 |
| JP | 2017-49030 A | | 3/2017 |
| JP | 2017-167047 A | | 9/2017 |
| JP | 2018-48842 A | | 3/2018 |
| WO | WO 2013/104954 A1 | | 7/2013 |
| WO | WO 2013/191273 A1 | | 12/2013 |
| WO | WO 2017/201055 A1 | | 11/2017 |
| WO | WO 2018/212364 A1 | | 11/2018 |

OTHER PUBLICATIONS

International Search Report issued on Jun. 30, 2020 in PCT/JP2020/014662 filed Mar. 30, 2020, 3 pages.
Extended European Search Report issued Nov. 29, 2022 in European Patent Application No. 20783998.6, 11 pages.
European Office Action issued Sep. 12, 2023, in European Patent Application No. 20 783 998.6, 10 pages.
Japanese Office Action issued Nov. 14, 2023 in Japanese Patent Application No. 2021-512130 (with unedited computer-generated English translation), 8 pages.
Combined Chinese Office Action and Search Report issued Jul. 28, 2023, in corresponding Chinese Patent Application No. 202080026121.7 (with English Translation), 26 pages.
Chinese Office Action issued Aug. 23, 2024 in Chinese Patent Application No. 202080026121.7 (with unedited, machine-generated English translation), 20 pages.
Chinese Office Action issued Jun. 14, 2024 in Chinese Patent Application No. 202080026121.7 (with unedited computer-generated English Translation), 14 pages.

* cited by examiner

LUBRICATING OIL DEGRADATION EVALUATION SYSTEM AND LUBRICATING OIL DEGRADATION EVALUATION METHOD

TECHNICAL FIELD

The present invention relates to a lubricating oil degradation evaluation system and a lubricating oil degradation evaluation method.

BACKGROUND ART

In order to appropriately manage a lubricating oil, it is important to accurately and quickly evaluate degradation and a contamination state of the lubricating oil. The degradation and contamination state of the lubricating oil has been conventionally evaluated by sampling a lubricating oil being used at a site, carrying this sample lubricating oil to a laboratory or the like in which the lubricating oil can be analyzed and evaluated, variously analyzing and evaluating the lubricating oil, and then evaluating the degradation and contamination state of the lubricating oil from those evaluation items.

The above evaluation method has disadvantages of requiring a large number of workers and a long time and lack of immediacy. In view of this, there is proposed a method of measuring a degree of degradation of a lubricating oil by using light transmission (see, for example, PTL 1).

CITATION LIST

Patent Literature

PTL 1: JP 2018-48842 A

SUMMARY OF INVENTION

Technical Problem

The method of measuring a degree of degradation of a lubricating oil by using light transmission proposed in, for example, PTL 1 requires a special imaging apparatus such as a hyperspectral camera that disperses light by each wavelength to perform imaging in order to evaluate the degree of degradation based on a spectral distribution. However, it is not realistic for a general user to possess the special imaging apparatus such as a hyperspectral camera because the special imaging apparatus is expensive. In other words, in order to use the method of measuring a degree of degradation of a lubricating oil by using light transmission proposed in, for example, PTL 1, it is necessary to bring a target lubricating oil into a laboratory or the like equipped with a special imaging apparatus such as a hyperspectral camera. Thus, it is still problematic to immediately evaluate the degradation and contamination state of the lubricating oil.

The present invention has been made in view of the above problems, and an object thereof is to provide a lubricating oil degradation evaluation system and a lubricating oil degradation evaluation method capable of immediately evaluating degradation and a contamination state of a lubricating oil.

Solution to Problem

Inventors of the present invention have diligently studied to solve the above problems, and, as a result, has found that degradation and a contamination state of a lubricating oil can be immediately evaluated by using imaging data captured by an imaging apparatus having a communication function possessed by a general user. That is, the present invention provides the following [1] to [12].

[1] A lubricating oil degradation evaluation system, including: a storage unit that stores evaluation reference data regarding evaluation of degradation of a lubricating oil; a creation unit that acquires imaging data of an evaluation lubricating oil serving as an evaluation target captured by an imaging apparatus having a communication function and creates image analysis data regarding degradation of the evaluation lubricating oil from the imaging data; and an evaluation unit that creates an evaluation result of a degree of degradation of the evaluation lubricating oil from the image analysis data on the basis of the evaluation reference data.

[2] The lubricating oil degradation evaluation system according to [1], in which the evaluation reference data includes at least one selected from the group consisting of color difference data, brightness data, color data, oil type data, new oil condition data, abrasion powder contamination data, and moisture contamination data.

[3] The lubricating oil degradation evaluation system according to [1] or [2], in which the imaging apparatus includes an imaging assistance device that specifies a distance from an imaging target and an angle of the imaging target.

[4] The lubricating oil degradation evaluation system according to any one of [1] to [3], in which the imaging data is obtained by imaging the evaluation lubricating oil serving as the evaluation target stored in a colorless light-transmitting container.

[5] The lubricating oil degradation evaluation system according to any one of [1] to [4], in which the creation unit includes correction data for correcting a wrong evaluation factor in the imaging data and creates the image analysis data from the imaging data corrected on the basis of the correction data.

[6] The lubricating oil degradation evaluation system according to any one of [1] to [5], in which the evaluation result includes an evaluation result of a remaining life of the evaluation lubricating oil.

[7] The lubricating oil degradation evaluation system according to any one of [1] to [6], further including a machine learning unit that processes an input variable extracted from the imaging data by a machine learning algorithm to derive a correlation between the evaluation of the degradation of the evaluation lubricating oil and the input variable and creates a prediction model for determining the image analysis data from the imaging data and the input variable, in which the creation unit creates the image analysis data from the prediction model and the imaging data.

[8] The lubricating oil degradation evaluation system according to [7], in which the input variable includes at least one selected from the group consisting of color difference data, brightness data, color data, oil type data, abrasion powder contamination data, and moisture contamination data.

[9] The lubricating oil degradation evaluation system according to [7] or [8], in which the algorithm includes at least one selected from the group consisting of support vector machine, linear regression, random forest, neural network, and gradient boosting decision tree.

[10] The lubricating oil degradation evaluation system according to any one of [7] to [9], in which each time creating the prediction model, the machine learning unit stores the created prediction model in the storage unit, and, when creating a new prediction model, performs machine learning by using the stored prediction model.

[11] A lubricating oil degradation evaluation method, including: a step of storing evaluation reference data regarding evaluation of degradation of a lubricating oil in a storage unit; a step of acquiring, in a creation unit, imaging data of an evaluation lubricating oil serving as an evaluation target captured by an imaging apparatus having a communication function and creating image analysis data regarding degradation of the evaluation lubricating oil from the imaging data; and a step of creating, in an evaluation unit, an evaluation result of a degree of degradation of the evaluation lubricating oil from the image analysis data on the basis of the evaluation reference data.

[12] The lubricating oil degradation evaluation method according to [11], further including a step of using, in a machine learning unit, a machine learning algorithm to derive a correlation between the evaluation of the degradation of the evaluation lubricating oil and an input variable extracted from the imaging data and creating a prediction model for determining the image analysis data from the imaging data and the input variable.

Advantageous Effects of Invention

The present invention can provide a lubricating oil degradation evaluation system and a lubricating oil degradation evaluation method capable of immediately evaluating degradation and a contamination state of a lubricating oil.

DESCRIPTION OF EMBODIMENTS

Hereinafter, there will be specifically described a lubricating oil degradation evaluation system and a lubricating oil degradation evaluation method according to each embodiment of the present invention (hereinafter, also simply referred to as "this embodiment"). Note that numerical values expressed by "or less", "or more", and "from . . . to . . . " regarding description of a range of numerical values in this specification can be arbitrarily combined, and numerical values in examples can be used as an upper limit value or lower limit value.

First Embodiment

[Lubricating Oil Degradation Evaluation System]

Figure 1:
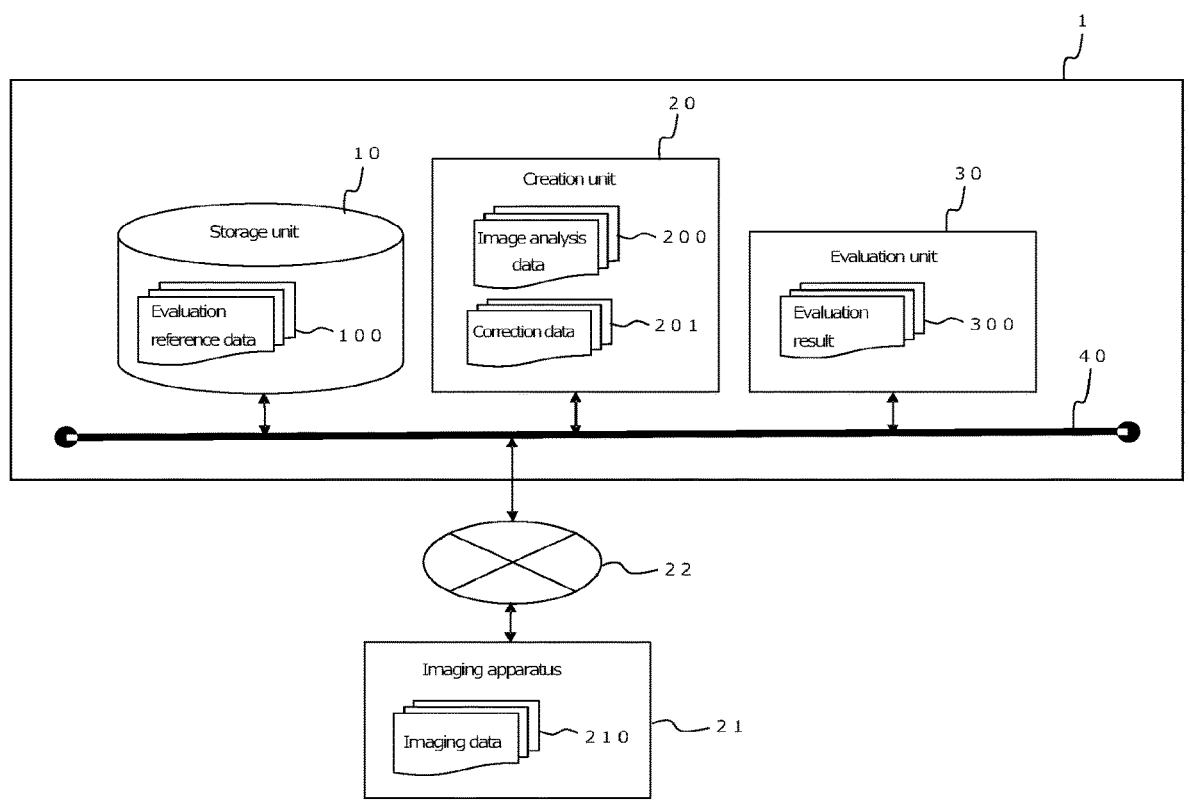
FIG. 1 is a schematic diagram of a lubricating oil degradation evaluation system according to a first embodiment of the present invention.

As illustrated in FIG. 1, a lubricating oil degradation evaluation system 1 according to a first embodiment of the present invention includes a storage unit 10, a creation unit 20, and an evaluation unit 30. Components of the lubricating oil degradation evaluation system 1 are connected by a system bus 40 and exchange data via the system bus 40.

<Storage Unit>

The storage unit 10 stores evaluation reference data 100 regarding evaluation of degradation of a lubricating oil. Means for storing the evaluation reference data 100 in the storage unit 10 can be a user interface of an information processing apparatus, and can be, for example, a mouse, keyboard, touchscreen, or voice input apparatus.

The storage unit 10 can be, for example, a storage medium such as a ROM, RAM, or hard disk.

The evaluation reference data 100 is data used as a reference for evaluating the degradation of the lubricating oil, such as color difference data, brightness data, color data, oil type data, new oil condition data, abrasion powder contamination data, and moisture contamination data.

The color difference data is data regarding a maximum color difference obtained by separating imaging data into color components (RGB values) and further separating the RGB values into 256 values. The maximum color difference is data obtained from a difference (MAX(R, G, B)−MIN(R, G, B)) between a maximum value and a minimum value of each of the RGB values (R value, G value, and B value). The color difference data includes data regarding an oil degradation threshold, which is expressed by the maximum color difference, for evaluating the degradation of the lubricating oil. The degradation of the lubricating oil is evaluated depending on whether or not the lubricating oil to be evaluated reaches the oil degradation threshold.

The brightness data is data regarding brightness obtained by separating the imaging data into the color components (RGB values) and further separating the RGB values into 256 values. The brightness ($\Delta E$) is data obtained by calculating $\Delta E = (R^2 + G^2 + B^2)^{1/2}$ by using the RGB values. The brightness data includes data regarding an oil degradation threshold, which is expressed by the brightness ($\Delta E$), for evaluating the degradation of the lubricating oil. The degradation of the lubricating oil is evaluated depending on whether or not the lubricating oil to be evaluated reaches the oil degradation threshold.

The color data is data obtained by measuring ASTM color according to JIS K 2580 (1993), Reference 1 Petroleum products—Determination of colour (stimulus value conversion method) 7.2. The color data includes data regarding an oil degradation threshold for evaluating the degradation of the lubricating oil. The degradation of the lubricating oil is evaluated depending on whether or not color of the lubricating oil to be evaluated reaches the oil degradation threshold.

The oil type data is data regarding the type of lubricating oil. The oil type data is data regarding an oil type such as an automobile oil, industrial lubricating oil, and marine lubricating oil, and includes data for specifying the oil type according to a product name, grade name, manufacturing time, manufacturing place, and the like. The oil type data is associated with an oil degradation threshold of each oil type and can therefore be used for evaluating whether or not the lubricating oil to be evaluated reaches the oil degradation threshold level.

The new oil condition data is data obtained when the lubricating oil is new. The new oil condition data is image data obtained when the lubricating oil is new, and is preferably image data obtained by imaging the new oil contained in a light-transmitting container (specific container). The new oil condition data includes data regarding an oil degradation threshold for evaluating the degradation of the lubricating oil on the basis of a difference in color obtained by comparing image data of the lubricating oil to be evaluated with the image data of the lubricating oil in a new condition. The degradation of the lubricating oil is evaluated depending on whether or not the difference in color of the lubricating oil to be evaluated reaches the oil degradation threshold.

The abrasion powder contamination data includes data regarding a contamination threshold for evaluating whether or not the lubricating oil is contaminated by abrasion powder. The degradation of the lubricating oil is evaluated depending on whether or not the lubricating oil to be evaluated reaches the contamination threshold. The abrasion powder contamination data serves as a reference data of non-uniformity generated in the image data in a case where the lubricating oil is contaminated due to mixing of the abrasion powder. The contamination threshold of the abrasion powder contamination data is set to, for exam-ple, 100 non-uniformity components/1 ml in the image data. When the lubricating oil exceeds this contamination threshold, it is possible to evaluate that the abrasion powder exists and contamination occurs.

The moisture contamination data includes data regarding a contamination threshold for evaluating whether or not the lubricating oil is contaminated by moisture exceeding solubility thereof. The degradation of the lubricating oil is evaluated depending on whether or not the lubricating oil to be evaluated reaches the contamination threshold. The moisture contamination data serves as a reference data of non-uniformity generated in the image data in a case where the lubricating oil is contaminated due to mixing of moisture exceeding the solubility. For example, in a case where there is a part in which layer separation occurs in the image data or one or more clouded parts caused by water droplets in the oil exist in the image data, it is possible to evaluate that contamination occurs due to moisture on the basis of the contamination threshold of the moisture contamination data.

<Creation Unit>

The creation unit 20 acquires imaging data 210 of an evaluation lubricating oil serving as an evaluation target captured by an imaging apparatus 21 having a communication function, and creates image analysis data 200 regarding the degradation of the evaluation lubricating oil from the imaging data 210.

The image analysis data 200 preferably includes at least data corresponding to the evaluation reference data 100 employed for evaluating the lubricating oil.

The imaging apparatus 21 is an apparatus that can acquire the imaging data 210 as image data of the evaluation lubricating oil to be evaluated by using an image sensor such as a CCD or CMOS. The imaging data 210 is preferably image data whose color tone and the like have not been processed, and is preferably unprocessed raw data that is original information on light captured by the image sensor.

The imaging apparatus 21 has a communication function and can therefore transmit the acquired imaging data 210 to the creation unit 20 of the lubricating oil degradation evaluation system 1 via a communication network 22. Examples of the communication network 22 include a wired or wireless local area network (LAN), wide area network (WAN), the Internet, intranet, and dedicated line. Examples of the imaging apparatus 21 having the communication function include a digital camera, portable terminal, and smartphone.

The imaging apparatus 21 preferably includes an imaging assistance device that specifies a distance from an imaging target and an angle of the imaging target in order to stably acquire the imaging data 210 of the evaluation lubricating oil serving as the evaluation target. The imaging assistance device is an assistance device which enables the imaging apparatus 21 to capture the imaging data 210 at the same angle of view and at a certain distance and angle between the imaging apparatus 21 and the evaluation lubricating oil serving as the evaluation target. Further, the imaging assistance device is an assistance device which enables the imaging apparatus 21 to perform imaging with the same amount of light at a certain distance and angle between the imaging apparatus 21 and backlight such as an LED. The imaging assistance device is preferably detached from/attached to the imaging apparatus 21 with ease, and preferably includes an engagement portion engageable with the imaging apparatus 21.

In order to stably acquire image data of the evaluation lubricating oil serving as the evaluation target, the imaging data 210 is preferably obtained by imaging the evaluation lubricating oil serving as the evaluation target stored in a colorless light-transmitting container (specific container).

In view of the above point, the light-transmitting container (specific container) can have any volume as long as the evaluation lubricating oil serving as the evaluation target can be uniformly sampled, and preferably has a certain volume of 0.1 ml or more but 10 ml or less, for example.

In view of the above point, it is preferable to have a constant length of light (optical path length) transmitting through the evaluation lubricating oil serving as the evaluation target when imaging is performed by using the light-transmitting container (specific container). For example, the optical path length is preferably 0.1 mm or more but 10 mm or less.

In view of the above point, a material of the light-transmitting container (specific container) preferably has high transmittance and can be, for example, glass, polycarbonate resin (PC), or acrylic resin (PMMA). The transmittance of the light-transmitting container (specific container) with a wavelength of 300 nm is preferably 70% or more, more preferably 75% or more, and further preferably 80% or more.

In order to eliminate a wrong evaluation factor such as dirt, it is preferable that a new light-transmitting container (specific container) be used each time imaging is performed.

The creation unit 20 includes correction data 201 for correcting a wrong evaluation factor in the imaging data 210, and preferably creates the image analysis data 200 from the imaging data 210 corrected on the basis of the correction data 201.

The correction data 201 is data for adjusting a white balance when the evaluation lubricating oil serving as the evaluation target is imaged and performing a correction for eliminating a wrong evaluation factor such as a color tone depending on an imaging environment. Further, the correction data 201 is data for making a correction to eliminate a wrong evaluation factor caused by dirt on a lens for use in imaging the evaluation lubricating oil serving as the evaluation target, the imaging assistance device, and the light-transmitting container (specific container).

Means for acquiring the correction data 201 is, for example, means for imaging a new or cleaned light-transmitting container (specific container) having no wrong evaluation factor such as dirt, thereby acquiring reference image data for making a correction to eliminate the wrong evaluation factor. Further, the means for acquiring the correction data 201 is, for example, to acquire reference image data as a part of the imaging data 210 when the imaging data 210 is acquired as the image data of the evaluation lubricating oil to be evaluated. Further, the means for acquiring the correction data 201 is, for example, to acquire a reference imaging data of the evaluation lubricating oil in a new condition at the same time when the imaging data 210 is acquired as the image data of the evaluation lubricating oil to be evaluated.

<Evaluation Unit>

The evaluation unit 30 creates an evaluation result 300 showing a degree of degradation of the evaluation lubricating oil from the image analysis data 200 on the basis of the evaluation reference data 100.

Examples of the evaluation result 300 include results of an overall evaluation of the degradation of the evaluation lubricating oil ("pass" or "failure"), an overall evaluation of contamination of the evaluation lubricating oil ("pass" or "failure"), the degree of degradation, and a degree of contamination.

The degree of degradation in the evaluation result 300 preferably includes an evaluation result of a remaining life of the evaluation lubricating oil. In a case where the evaluation result 300 includes the evaluation result of the remaining life, it is possible to make notification of the time to replace the oil.

Lubricating Oil Degradation Evaluation Method

Figure 2:
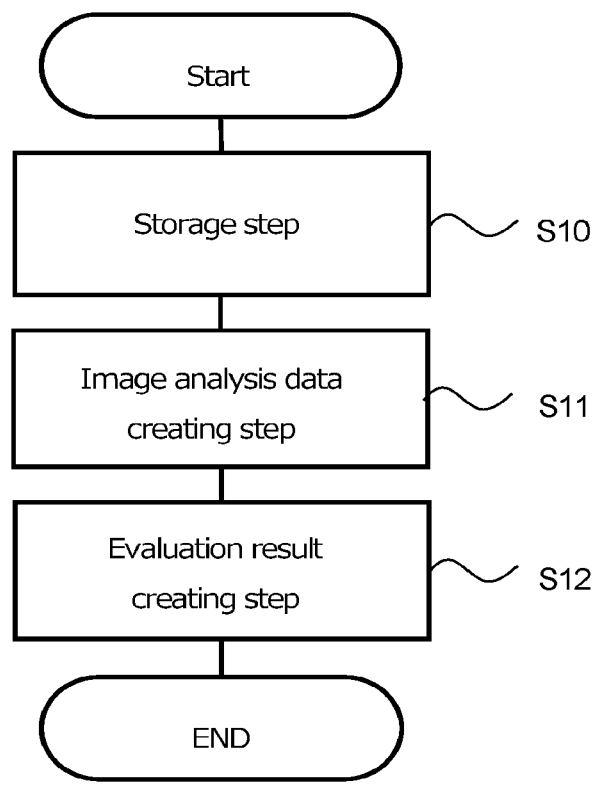
FIG. 2 is a flowchart of a lubricating oil degradation evaluation method according to the first embodiment of the present invention.

As illustrated in FIG. 2, a lubricating oil degradation evaluation method according to the first embodiment of the present invention includes a storage step S10, an image analysis data creating step S11, and an evaluation result creating step S12. Hereinafter, the lubricating oil degradation evaluation method according to the first embodiment of the present invention will be described with reference to FIGS. 1 and 2.

<Storage Step>

In the storage step S10, the evaluation reference data 100 regarding the evaluation of the degradation of the lubricating oil is stored in the storage unit 10. A method of storing the data in the storage unit 10 is, for example, to input the evaluation reference data 100 by using an input unit (not illustrated) such as the user interface of the information processing apparatus, thereby storing the data.

<Image Analysis Data Creating Step>

In the image analysis data creating step S11, the imaging data 210 of the evaluation lubricating oil serving as the evaluation target captured by the imaging apparatus 21 having the communication function is acquired, and the image analysis data 200 regarding the degradation of the evaluation lubricating oil is created in the creation unit 20 from the imaging data 210.

Specifically, first, the imaging apparatus 21 images the imaging data 210 of the evaluation lubricating oil serving as the evaluation target. Then, the imaging apparatus 21 having the communication function transmits the acquired imaging data 210 to the lubricating oil degradation evaluation system 1 via the communication network 22.

Then, the creation unit 20 acquires the imaging data 210 of the evaluation lubricating oil serving as the evaluation target captured by the imaging apparatus 21 having the communication function.

Then, the creation unit 20 creates the image analysis data 200 regarding the degradation of the evaluation lubricating oil from the acquired imaging data 210. The created image analysis data 200 is stored in the storage unit 10. In a case where the image analysis data 200 is created, the creation unit 20 preferably acquires the correction data 201 for correcting a wrong evaluation factor in the imaging data 210 and creates the image analysis data 200 from the imaging data 210 corrected on the basis of the correction data 201.

<Evaluation Result Creating Step>

In the evaluation result creating step S12, the evaluation result 300 regarding the degree of degradation of the evaluation lubricating oil is created in the evaluation unit 30 from the image analysis data 200 on the basis of the evaluation reference data 100.

Specifically, first, the evaluation unit 30 associates the evaluation reference data 100 and the image analysis data 200 stored in the storage unit 10 according to the oil type or the like, and compares the image analysis data 200 with the evaluation reference data 100, thereby creating the evaluation result 300 regarding the degree of degradation of the evaluation lubricating oil. The evaluation result 300 preferably includes the evaluation result of the remaining life of the evaluation lubricating oil.

The evaluation unit 30 stores the created evaluation result 300 in the storage unit 10. The evaluation result 300 can be output to an output unit (not illustrated) of a user terminal or the like via the communication network 22.

According to the lubricating oil degradation evaluation system and the lubricating oil degradation evaluation method according to the first embodiment of the present invention, it is possible to immediately evaluate degradation and a contamination state of a lubricating oil by using imaging data captured by an imaging apparatus having a communication function possessed by a general user.

Second Embodiment

[Lubricating Oil Degradation Evaluation System]

Figure 3:
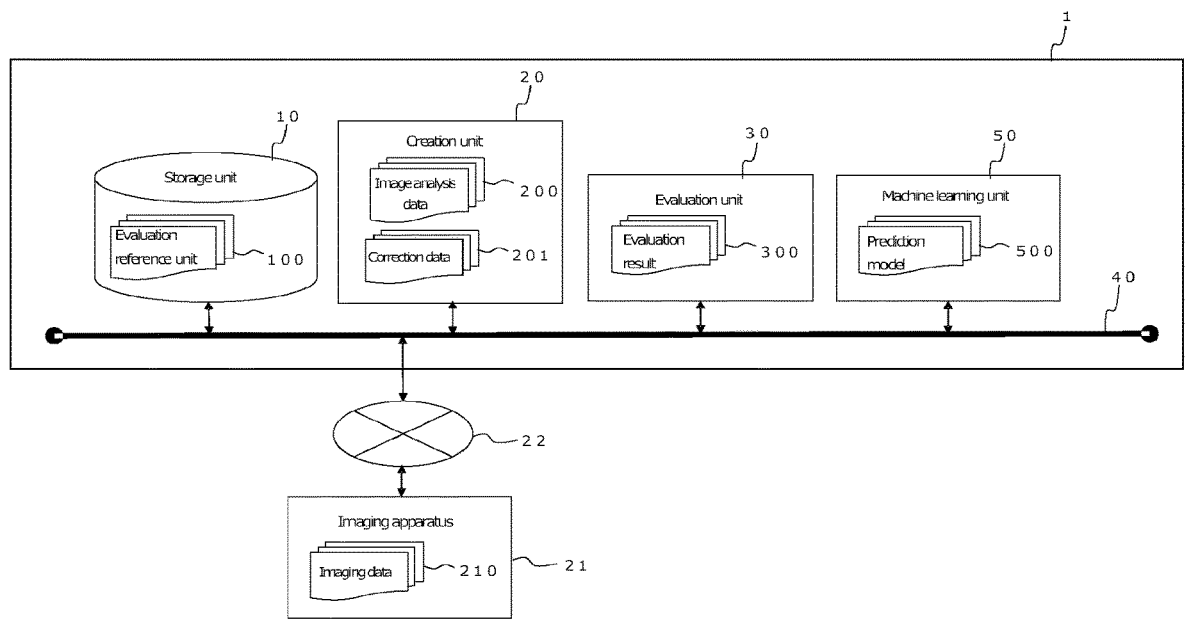
FIG. 3 is a schematic diagram of a lubricating oil degradation evaluation system according to a second embodiment of the present invention.

As illustrated in FIG. 3, a lubricating oil degradation evaluation system 1 according to a second embodiment of the present invention includes a storage unit 10, a creation unit 20, and an evaluation unit 30, and further includes a machine learning unit 50. Components of the lubricating oil degradation evaluation system 1 are connected by a system bus 40 and exchange data via the system bus 40.

Description of the same components as those in the lubricating oil degradation evaluation system 1 according to the first embodiment will be omitted.

<Machine Learning Unit>

The machine learning unit 50 processes an input variable extracted from imaging data 210 by a machine learning algorithm to derive a correlation between evaluation of degradation of an evaluation lubricating oil and the input variable, thereby creating a prediction model 500 for determining image analysis data 200 from the imaging data 210 and the input variable. The prediction model 500 is created in such a way that the machine learning unit 50 evaluates a degree of importance of each extracted input variable regarding the evaluation of the degradation of the evaluation lubricating oil on the basis of the correlation between the evaluation of the degradation of the evaluation lubricating oil and the input variable, and sets a parameter for each input variable in accordance with the degree of importance.

It is preferable that the machine learning unit 50 also derive a correlation between the input variable and the evaluation of the degradation of the evaluation lubricating oil, the correlation being caused by an individual difference in an imaging apparatus 21 and an imaging environment, and reflect the correlation in the prediction model 500.

The input variable used by the machine learning unit 50 can be similar to the above evaluation reference data 100. Examples thereof include color difference data, brightness data, color data, oil type data, new oil condition data, abrasion powder contamination data, and moisture contamination data, and the input variable preferably includes at least one selected from the above data. In particular, the input variable more preferably includes at least one selected from the color difference data, the brightness data, the color data, the oil type data, the abrasion powder contamination data, and the moisture contamination data.

Examples of the algorithm of the machine learning unit 50 include support vector machine, linear regression, random forest, neural network, and gradient boosting decision tree, and the algorithm preferably includes at least one selected from the above algorithms.

Each time creating the prediction model 500, the machine learning unit 50 stores the created prediction model 500 in the storage unit 10, and, when creating a new prediction model 500, performs machine learning by using the stored prediction model 500.

<Creation Unit>

The creation unit 20 of the lubricating oil degradation evaluation system 1 according to the second embodiment of the present invention preferably creates the image analysis data 200 from the prediction model 500 and the imaging data 210.

[Lubricating Oil Degradation Evaluation Method]

Figure 4:
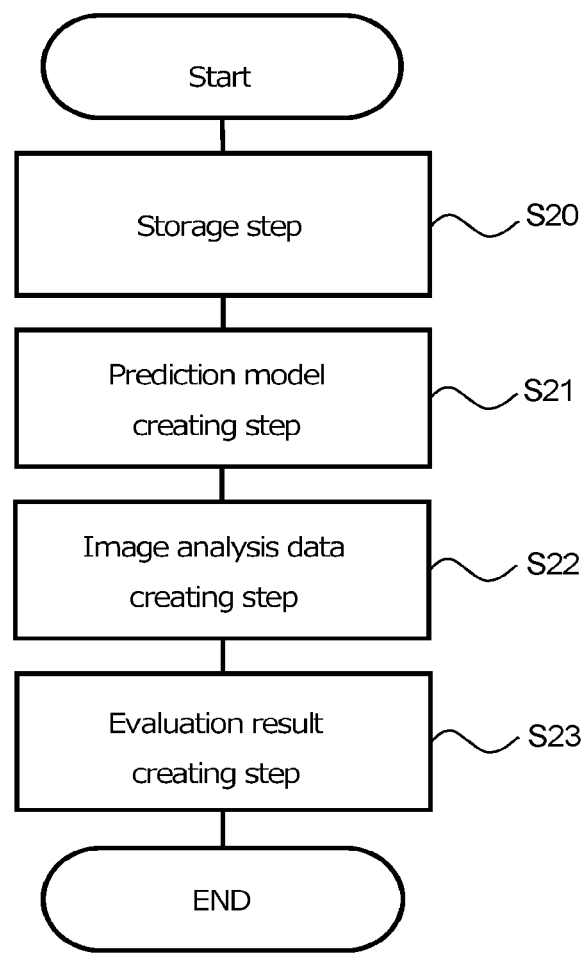
FIG. 4 is a flowchart of a lubricating oil degradation evaluation method according to the second embodiment of the present invention.

As illustrated in FIG. 4, a lubricating oil degradation evaluation method according to the second embodiment of the present invention includes a storage step S20, a prediction model creating step S21, an image analysis data creating step S21, and an evaluation result creating step S23. Hereinafter, the lubricating oil degradation evaluation method according to the second embodiment of the present invention will be described with reference to FIGS. 3 and 4.

<Storage Step>

In the storage step S20, evaluation reference data 100 regarding the evaluation of the degradation of the lubricating oil is stored in the storage unit 10. A method of storing the data in the storage unit 10 is, for example, to input the evaluation reference data 100 by using an input unit (not illustrated) such as a user interface of an information processing apparatus, thereby storing the data.

<Prediction Model Creating Step>

In the prediction model creating step S21, the input variable extracted from the imaging data 210 is processed by the machine learning algorithm to derive the correlation between the evaluation of the degradation of the evaluation lubricating oil and the input variable, thereby the prediction model 500 for determining the image analysis data 200 from the imaging data 210 and the input variable is created in the machine learning unit 50.

Specifically, first, the machine learning unit 50 refers to the imaging data 210 stored in the storage unit 10, and extracts the input variable from the imaging data 210.

Then, the machine learning unit 50 processes the extracted input variable by the machine learning algorithm to derive the correlation between the evaluation of the degradation of the evaluation lubricating oil and the input variable. That is, the machine learning unit 50 uses the machine learning algorithm to derive the input variable having a high degree of importance as a factor of the evaluation of the degradation of the evaluation lubricating oil. Then, the machine learning unit 50 creates the prediction model 500 in which a parameter for each input variable is set according to the degree of importance.

Each time creating the prediction model 500, the machine learning unit 50 can store the created prediction model 500 in the storage unit 10, and, when creating the prediction model 500, can perform machine learning by using the stored prediction model 500.

<Image Analysis Data Creating Step>

In the image analysis data creating step S22, the imaging data 210 of the evaluation lubricating oil serving as the evaluation target captured by the imaging apparatus 21 having the communication function is acquired, then the prediction model 500 created in the machine learning unit 50 is acquired, and the image analysis data 200 regarding the degradation of the evaluation lubricating oil is created in the creation unit 20 from the imaging data 210 and the prediction model 500.

Specifically, first, the imaging apparatus 21 captured the imaging data 210 of the evaluation lubricating oil serving as the evaluation target. Then, the imaging apparatus 21 having the communication function transmits the acquired imaging data 210 to the lubricating oil degradation evaluation system 1 via a communication network 22.

Then, the creation unit 20 acquires the imaging data 210 of the evaluation lubricating oil serving as the evaluation target captured by the imaging apparatus 21 having the communication function.

Then, the creation unit 20 acquires the prediction model 500 stored in the storage unit 10.

Then, the creation unit 20 creates the image analysis data 200 regarding the degradation of the evaluation lubricating oil from the acquired imaging data 210 and prediction model 500. The created image analysis data 200 is stored in the storage unit 10. In a case where the image analysis data 200 is created, the creation unit 20 preferably acquires correction data 201 for correcting a wrong evaluation factor in the imaging data 210 and creates the image analysis data 200 from the imaging data 210 corrected on the basis of the correction data 201.

<Evaluation Result Creating Step>

In the evaluation result creating step S23, an evaluation result 300 regarding the degree of degradation of the evaluation lubricating oil is created in the evaluation unit 30 from the image analysis data 200 on the basis of the evaluation reference data 100.

Specifically, first, the evaluation unit 30 associates the evaluation reference data 100 and the image analysis data 200 stored in the storage unit 10 according to the oil type or the like, and compares the image analysis data 200 with the evaluation reference data 100, thereby creating the evaluation result 300 regarding the degree of degradation of the evaluation lubricating oil. The evaluation result 300 preferably includes an evaluation result of a remaining life of the evaluation lubricating oil.

The evaluation unit 30 stores the created evaluation result 300 in the storage unit 10. The evaluation result 300 can be output to the output unit (not illustrated) of a user terminal or the like via the communication network 22.

According to the lubricating oil degradation evaluation system and the lubricating oil degradation evaluation method according to the second embodiment of the present invention, it is possible to immediately evaluate degradation and a contamination state of a lubricating oil by using imaging data captured by an imaging apparatus having a communication function possessed by a general user.

Further, according to the lubricating oil degradation evaluation system and the lubricating oil degradation evaluation method according to the second embodiment of the present invention, it is possible to perform evaluation regarding the degradation and contamination state of the lubricating oil with high accuracy by performing machine learning.

EXAMPLES

Next, the present invention will be further specifically described with reference to examples. However, the present invention is not limited in any way by those examples.
(Acquisition of Evaluation Reference Data)
The following test was performed to acquire evaluation reference data serving as a reference for evaluating a degradation state of a lubricating oil.
(1) Test Oil
The following sample oils A to C were used as a model processed oil for the evaluation reference data.

Base oil (150N mineral oil (62.54 mass %)+500N mineral oil (36.00 mass %): kinematic viscosity at 40° C.=47.61 mm$^2$/s, kinematic viscosity at 100° C.=7.156 mm$^2$/s, and index of viscosity=109)     a) Sample oil A Additives: antioxidant, rust inhibitor, pour point depressant, detergent dispersant, extreme pressure agent, demulsifier, and anti-foaming agent contained in a total amount of 1.46 mass % based on the total amount of the sample oil Base oil (150N mineral oil (64.95 mass %)+500N mineral oil (33.85 mass %): kinematic viscosity at 40° C.=44.39 mm$^2$/s, kinematic viscosity at 100° C.=6.855 mm$^2$/s, and index of viscosity=110)     b) Sample oil B Additives: antioxidant, rust inhibitor, pour point depressant, detergent dispersant, extreme pressure agent, demulsifier, and anti-foaming agent contained in a total amount of 1.20 mass % based on the total amount of the sample oil Base oil (150N mineral oil (63.57 mass %)+500N mineral oil (31.92 mass %): kinematic viscosity at 40° C.=44.90 mm$^2$/s, kinematic viscosity at 100° C.=6.882 mm$^2$/s, and index of viscosity=109)     c) sample oil C Additives: antioxidant, rust inhibitor, pour point depressant, detergent dispersant, extreme pressure agent, demulsifier, and anti-foaming agent contained in a total amount of 4.51 mass % based on the total amount of the sample oil The above data was stored in the storage unit 10 of FIG. 1 as the oil type data.
(2) Imaging Data
Each sample oil was poured into a glass container (transmittance: 90%) having an internal volume of 5 ml. Image data (imaging data) captured from a side surface of the above glass container by using a smartphone equipped with a built-in camera of twelve million effective pixels was separated into components (RGB values). The above data was associated with the above oil type data and was stored in the storage unit 10 as the new oil condition data.
(3) Degradation Test (ISOT Test)
In the presence of copper and iron catalyzers in each sample oil, the sample oil was degraded at a test temperature of 130° C. for a test time of 168 hours in conformity to JIS K 2514-1:2013. At that time, image data (imaging data) of each sample oil was captured by using a glass container and smartphone similar to the above ones when 48 hours, 96 hours, and 168 hours passed from the new oil. Then, the image data was separated into components (RGB values) and was stored in the storage unit 10.

Further, the sample oil degraded for the above each time was tested in conformity to the rotating bomb oxidation test in JIS K 2514-3:2013 at a test temperature of 150° C. under a pressure of 620 kPa, thereby measuring a time (RBOT value, Rt) until the pressure was reduced by 175 kPa from a maximum pressure. Further, a RBOT value (R0) obtained by degrading each sample oil until the remaining life thereof became 0 hours was also measured. Then, a residual percentage of RBOT was obtained from the following expression by using the above RBOT values and a RBOT value (Rn) of the new oil.

$$\text{Residual percentage of RBOT (\%)} = [Rt/(Rn-R0)] \times 100$$

The above image data, degradation test condition, residual percentage of RBOT, and remaining life of the new oil were associated with the oil type data and were stored in the storage unit 10.

The above data (2) and (3) are collectively shown in Table 1. Note that an index of degradation in Table 1 was obtained from the above residual percentage of RBOT in consideration of an amount of increase in acid value, an amount of moisture, and an amount of impurities as an example.

TABLE 1

|  | Sample oil A Elapsed time | | | | Sample oil B Elapsed time | | | | Sample oil C Elapsed time | | | |
| --- | --- | --- | --- | --- | --- | --- | --- | --- | --- | --- | --- | --- |
|  | New oil | 48 h | 96 h | 168 h | New oil | 48 h | 96 h | 168 h | New oil | 48 h | 96 h | 168 h |
| R | 255 | 255 | 255 | 253 | 255 | 243 | 232 | 121 | 255 | 246 | 133 | 74 |
| G | 255 | 216 | 181 | 136 | 255 | 215 | 160 | 40 | 255 | 129 | 31 | 29 |
| B | 255 | 34 | 14 | 5 | 255 | 65 | 24 | 7 | 255 | 16 | 12 | 5 |
| Residual percentage of RBOT (%) | 100 | 92 | 73 | 47 | 100 | 62 | 46 | 33 | 100 | 36 | 22 | 13 |
| Index of degradation | 10 | 9 | 7 | 5 | 10 | 6 | 5 | 3 | 10 | 4 | 2 | 1 |
| Remaining life (h) | 288 | 240 | 192 | 120 | 216 | 168 | 120 | 48 | 120 | 72 | 24 | 0 |

Example 1

The sample oil B was subjected to a real machine equivalent degradation test by continuously driving a rotary compressor in the presence of the sample oil at an average driving oil temperature of 80° C. under an average driving pressure of 35 MPa while supplying air at 1.0 L/h in conformity to JIS K2514:2013. At that time, image data (imaging data) of each sample oil was obtained by using a glass container and smartphone similar to the above ones when the test was performed for 100 hours, 200 hours, 300 hours, and 400 hours from the new oil. Then, the above image data was separated into components (RGB values) and was transmitted to the lubricating oil degradation evaluation system.

Note that, at that time, oil type data and a degradation test condition of the sample oil B were also transmitted to the lubricating oil degradation evaluation system.

In the lubricating oil degradation evaluation system 1 of FIG. 1, first, the image analysis data 200 regarding degradation of the evaluation sample oil is created from the acquired image data in the creation unit 20. The created image analysis data 200 is stored in the storage unit 10. Next, in the evaluation unit 30, a degree of degradation of each sample oil is created as the evaluation result 300 from the image analysis data 200 on the basis of the evaluation reference data 100.

Specifically, first, the evaluation unit 30 associates the evaluation reference data 100 and the image analysis data 200 stored in the storage unit 10 according to the oil type data. Then, the evaluation result 300 regarding the degree of degradation of the evaluation sample oil is created by comparing the image analysis data 200 with the evaluation reference data 100 and further referring to the degradation test condition. The evaluation result 300 includes the residual percentage of RBOT (residual percentage of estimated life) of the evaluation sample oil.

The evaluation unit 30 stores the created evaluation result 300 in the storage unit 10. The evaluation result 300 is output to the user terminal via the communication network. Results thereof are collectively shown in Table 2.

Example 2

As in Example 1, image data (imaging data) was obtained by subjecting the sample oil B to a degradation test in a similar condition, was separated into components (RGB values), and was transmitted to the lubricating oil degradation evaluation system. Further, a remaining life (hour) of each of the new sample oil B was also transmitted to the lubricating oil degradation evaluation system.

In the evaluation unit 30 of the lubricating oil degradation evaluation system 1, a degree of degradation of each sample oil is created as an evaluation result 300' from the image analysis data 200 on the basis of the evaluation reference data 100 in a similar way to Example 1.

Specifically, first, the evaluation unit 30 creates the evaluation result 300' regarding the degree of degradation of the evaluation lubricating oil by comparing the image analysis data 200 stored in the storage unit 10 with the evaluation reference data 100 and further referring to the remaining life of the new oil and the degradation test condition. The evaluation result 300' includes the remaining life of the evaluation sample oil.

The evaluation unit 30 stores the created evaluation result 300' in the storage unit 10. The evaluation result 300' is output to the user terminal via the communication network. Results thereof are collectively shown in Table 2.

TABLE 2

| | Sample oil B Elapsed time | | | | |
|---|---|---|---|---|---|
| | New oil | 100 h | 200 h | 300 h | 400 h |
| R | 255 | 255 | 236 | 198 | 157 |
| G | 255 | 253 | 169 | 92 | 38 |

TABLE 2-continued

| | Sample oil B Elapsed time | | | | |
|---|---|---|---|---|---|
| | New oil | 100 h | 200 h | 300 h | 400 h |
| B | 255 | 2 | 1 | 2 | 0 |
| Residual percentage of RBOT (%) | 100 | 95 | 78 | 41 | 32 |
| index of degradation | 10 | 9 | 7 | 4 | 3 |
| Remaining life (h) | 600 | 500 | 400 | 300 | 200 |

INDUSTRIAL APPLICABILITY

The lubricating oil degradation evaluation system and the lubricating oil degradation evaluation method according to the embodiments can evaluate degradation and a contamination state of a lubricating oil by using imaging data captured by an imaging apparatus having a communication function possessed by a general user. This makes it possible for the general user to easily evaluate degradation of the lubricating oil.

REFERENCE SIGNS LIST

1: lubricating oil degradation evaluation system
10: storage unit
20: creation unit
21: imaging apparatus
22: communication network
30: evaluation unit
40: system bus
50: machine learning unit

The invention claimed is:
1. A lubricating oil degradation evaluation system, comprising:
a storage unit that stores evaluation reference data regarding evaluation of degradation of a lubricating oil;
a creation unit that acquires imaging data of an evaluation lubricating oil serving as an evaluation target captured by an imaging apparatus having a communication function and creates image analysis data regarding degradation of the evaluation lubricating oil from the imaging data;
an evaluation unit that creates an evaluation result of a degree of degradation of the evaluation lubricating oil from the image analysis data on the basis of the evaluation reference data; and
a machine learning unit that processes an input variable extracted from the imaging data by a machine learning algorithm to derive a correlation between the evaluation of the degradation of the evaluation lubricating oil and the input variable and creates a prediction model for determining the image analysis data from the imaging data and the input variable, wherein
the evaluation reference data includes oil type data,
the oil type data is associated with an oil degradation threshold of each oil type and is used for evaluating whether or not the lubricating oil to be evaluated reaches the oil degradation threshold level,
the creation unit comprises correction data for correcting a wrong evaluation factor in the imaging data and creates the image analysis data from the imaging data corrected on the basis of the correction data,
the creation unit creates the image analysis data from the prediction model and the imaging data, the input variable comprises at least one selected from the group consisting of color difference data, brightness data, color data, oil type data, abrasion powder contamination data, and moisture contamination data, the machine learning algorithm comprises at least one selected from the group consisting of support vector machine, linear regression, random forest, neural network, and gradient boosting decision tree, and each time the machine learning unit creates the prediction model, the machine learning unit stores the created prediction model in the storage unit, and, when creating a new prediction model, performs machine learning by using the stored prediction model.

2. The lubricating oil degradation evaluation system according to claim 1, wherein the evaluation reference data further comprises at least one selected from the group consisting of color difference data, brightness data, color data, new oil condition data, abrasion powder contamination data, and moisture contamination data.

3. The lubricating oil degradation evaluation system according to claim 1, wherein the imaging apparatus comprises an imaging assistance device that specifies a distance from an imaging target and an angle of the imaging target.

4. The lubricating oil degradation evaluation system according to claim 1, wherein the imaging data is obtained by imaging the evaluation lubricating oil serving as the evaluation target stored in a colorless light-transmitting container.

5. The lubricating oil degradation evaluation system according to claim 1, wherein the evaluation result comprises an evaluation result of a remaining life of the evaluation lubricating oil.

6. A lubricating oil degradation evaluation method, comprising:

storing evaluation reference data regarding evaluation of degradation of a lubricating oil in a storage unit;

processing, in a machine learning unit, an input variable extracted from imaging data by a machine learning algorithm to derive a correlation between an evaluation of the degradation of the evaluation lubricating oil and the input variable, and creating a prediction model for determining image analysis data from the imaging data and the input variable, and storing the created prediction model in the storage unit;

acquiring, in a creation unit, the imaging data of an evaluation lubricating oil serving as an evaluation target captured by an imaging apparatus having a communication function and creating image analysis data regarding degradation of the evaluation lubricating oil from the imaging data and the prediction model; and creating, in an evaluation unit, an evaluation result of a degree of degradation of the evaluation lubricating oil from the image analysis data on the basis of the evaluation reference data, wherein the evaluation reference data includes oil type data associated with an oil degradation threshold of each oil type and the creating he evaluation result includes evaluating whether or not the lubricating oil evaluated reaches the oil degradation threshold level, the creation unit comprises correction data for correcting a wrong evaluation factor in the imaging data and creates the image analysis data from the imaging data corrected on the basis of the correction data, the input variable comprises at least one selected from the group consisting of color difference data, brightness data, color data, oil type data, abrasion powder contamination data, and moisture contamination data, the machine learning algorithm comprises at least one selected from the group consisting of support vector machine, linear regression, random forest, neural network, and gradient boosting decision tree, and when creating a new prediction model, the machine learning unit performs machine learning by using the stored prediction model.

* * * * *